United States Patent [19]
Lakowicz et al.

[11] Patent Number: 5,504,337
[45] Date of Patent: Apr. 2, 1996

[54] METHOD AND APPARATUS FOR PERFORMING PHASE FLUORESCENCE LIFETIME MEASUREMENTS IN FLOW CYTOMETRY

[75] Inventors: Joseph R. Lakowicz, 10037 Fox Den Rd., Ellicott City, Md. 21042; Klaus W. Berndt, Baltimore, Md.; Robert A. Hoffman, Livermore; Bertram G. Pinsky, Hayward, both of Calif.

[73] Assignee: Joseph R. Lakowicz, Ellicott City, Md.

[21] Appl. No.: 50,122

[22] PCT Filed: Oct. 10, 1991

[86] PCT No.: PCT/US91/07259

§ 371 Date: Apr. 12, 1993

§ 102(e) Date: Apr. 12, 1993

[87] PCT Pub. No.: WO92/07245

PCT Pub. Date: Apr. 30, 1992

Related U.S. Application Data

[63] Continuation-in-part of Ser. No. 595,343, Oct. 10, 1990, abandoned.

[51] Int. Cl.[6] .................................................. G01N 21/64
[52] U.S. Cl. .................................. 250/461.2; 250/459.1; 356/318
[58] Field of Search ........................... 250/461.2, 458.1, 250/459.1; 356/318, 417; 436/172

[56] References Cited

U.S. PATENT DOCUMENTS 5,315,122   5/1994   Pinsky et al. ............... 250/461.2
5,317,162   5/1994   Pinsky et al. ............... 250/461.2

Primary Examiner—Davis L. Willis
Assistant Examiner—Richard Hanig
Attorney, Agent, or Firm—Rothwell, Figg, Ernst & Kurz

[57] ABSTRACT

A method and apparatus for identifying individual particles or cells which have been labeled with different fluorochromes, on the basis of the lifetime of their fluorescence, or based on different decay times for a fluorochrome in different cells.

18 Claims, 9 Drawing Sheets

1

METHOD AND APPARATUS FOR PERFORMING PHASE FLUORESCENCE LIFETIME MEASUREMENTS IN FLOW CYTOMETRY

This application is a continuation-in-part of application Ser. No. 07/595,343, filed Oct. 10, 1990, now abandoned.

BACKGROUND OF THE INVENTION

The present invention relates to a flow cytometry method and apparatus for distinguishing and/or characterizing cells or particles on the basis of measured fluorescence lifetimes. More particularly, the present invention concerns a flow cytometry method and apparatus for distinguishing and characterizing a particle or cell which has been labeled or associated with one or more fluorophores having lifetimes which are modified due to one or more characteristics or properties of a cell or particle with which the fluorophore is associated, wherein the lifetime measurments are independent of the intensity of the detected fluorescence emission.

Research involving the study and analysis of cells, generally known as cytology, employs a variety of analytical techniques for identifying and enumerating the subpopulations of cells in a specimen under study. For example, cytological materials may be examined to detect the presence of cancerous or malignant cells, or characteristics of the cells within a specimen. For purposes of analysis, the cells may be labeled with a variety of fluorescent materials, conventionally known as fluorophores or fluorescent probes, which have an identified affinity for cells or cell components which are of interest to an analysis. The fluorophores will emit a particular fluorescence radiation when stimulated by light at a wavelength corresponding to the excitation wavelength of the fluorophore. The wavelength and/or intensity of the emitted light has been used to analyze a subpopulation of cells, wherein different fluorophores can be used to distinguish subpopulations of fluorophore-labeled cells.

The study of collections of multiple cells using fluorescent spectroscopy has obvious limitations. For example, an accurate determination of the number of cells in a subpopulation having a given characteristic cannot be made and, more importantly, the subpopulations cannot be separated for further analysis. In order to permit the measurement and analysis of a population of cells (or any biological particle such as isolated nuclei, chromosome preparations or neurobiological organisms) on an individual basis, fluorescence flow cytometry has been employed.

Fluorescence flow cytometry, which involves the intensity and/or wavelength measurement of fluorescence emissions from individual cells labeled with a fluorophore while the cells are flowing in a liquid or gaseous medium past an observation point, permits analysis of individual cells as well as sorting of the cells based upon that analysis. A description of examples of fluorescence flow cytometry appears in "Practical Flow Cytometry", 2d. ed., H. Shapiro (1988), Liss & Co, the entire contents of which are herein incorporated by reference.

A conventional flow cytometer has a sample handling and delivery system which collects the cell population into a stream of individual cells which is directed one cell at a time past the observation point of the flow cytometer. When a liquid medium is used, the stream containing the samples is sheathed by a surrounding fluid stream to insure that only single cells pass the observation point.

A conventional flow cytometer also has a parameter detection system which can include a focused light source, typically a laser, that directs a narrow beam of light at a predetermined wavelength to the observation point where an individual fluorophore-labeled cell passing through the point may be illuminated, resulting in a fluorescence emission from the fluorophore label. The parameter detection system also includes collection optics and optical transducers, such as photomultipliers and detectors that receive the fluorescence emission at the observation point and convert it to electrical signals which are representative of the intensity and/or wavelength of the emitted light.

Where the cells have been tagged with a fluorophore having an affinity for a particular characteristic or composition of the cell, as well as being excited at the wavelength of light emitted by the laser, the light emission intensity and/or wavelength of the fluorophore bound to each cell at the observation point may be detected for purposes of analysis.

When the fluorophore bound to a cell is excited by light at the fluorophore's absorption wavelength, the fluorophore's electrons can absorb energy such that the energy level of an electron is raised from the ground state to an excited state. The excited electron then emits a photon as it returns to the ground state, with the photon having a characteristic wavelength and intensity.

In FIG. 1 is shown an advanced streak camera flow cytometry apparatus. The pulsed output from the light source 1 passes through an optics subsystem 2 where it is shaped and focused into the continuous flow of cells or particles. The cells are in a suspension from sample source 4 and are aligned within sample chamber 5 by the laminar flow of a fluid sheath from a solution source 6. When the laser light illuminates an individual cell at the observation point in a flow chamber 3, a fluorescence is emitted as pulsed fluorescence radiation 7. This pulsed radiation is captured by an optics subsystem 8 and focused onto the streak camera detector 9. The output of the detector is a voltage that is applied by line 16 to a signal processing system 10 where it is used for cell population analysis based on intensity and/or wavelength of the emitted fluorescence. The signal processing is fast enough to control the division of the observed cells into subpopulation collections by a conventional cell sorter 11.

Thus, measurements of the intensity and/or wavelength of emitted fluorescence over a period of time may be used as the basis for discrimination and sorting of the cells or particles in the population under study, and the intensity of emitted light may be measured by photomultipliers.

Several conventional methods for distinguishing cells by detecting the emitted fluorescence light at the observation point of a flow cytometer system are known. The advanced streak camera system of FIG. 1 measures for each cell the change in the intensity of transient emitted light over a period of time as the cell passed through the laser beam. Based upon such measurements, the attenuation time of the emitted light, the rise time of the emitted light and the orientation relaxation time may be detected and used as a basis for cell discrimination. Referring again to FIG. 1, the attenuation time of the emitted light (i.e. the fluorescence lifetime, representing the average amount of time a molecule remains in the excited state prior to returning to a ground state) is determined based on the intensity of the fluorescence emission, using the output of streak camera 9 on a cell-by-cell basis. The output from camera 9 and a peak threshold value 12a are input to comparator 13, and, when a decreasing light emission signal reaches the peak threshold value, a counter 15 is started and continues to count until the light emission signal reaches an attenuation threshold value 14 (typically 1/e or 63% of peak) when the count is terminated. The processor 10 uses the attenuation time count for each cell to perform an analysis of the sample cell population and even control cell sorting with sorter 11.

However, this streak camera approach encounters significant difficulties due to the need for highly accurate and expensive counters. Also, this approach is dependent on the intensity of the emitted light, which will require the peak threshold to be varied. Moreover, if variable signal attenuation is present, due to the dependence of the count on emitted light intensity, the measuring of attenuation time may not be consistent. Furthermore, the use of a synchroscan streak camera has the disadvantage of high cost, high complexity and limited sensitivity, owing to its extremely small sensitive area.

In a similar intensity-based system disclosed in U.S. Pat. No. 4,778,539, Yamashita et al, issued Oct. 18, 1988, individual cells may be distinguished by measuring light at an observation point of a flow cytometer system. There, the change in the intensity of transient emitted light over a period of time, following excitation by short pulses of laser light, may be measured and used to detect the attenuation time of the emitted light, the rise time of the emitted light and the orientation relaxation time. These parameters may be used as a basis for cell discrimination. However, such measurements are intensity-based and are performed cell-by-cell, and do not allow for rapid and/or simultaneous scanning of a population of cells, based on lifetime measurements.

A suggestion that phase based measurement of fluorescence lifetimes may be employed in flow cytometric systems appears in Cytometry, Supplement 2, p. 91 (1988), Steincamp et al. However, there is no specific disclosure of the structure or method of operation of a system which can perform the identified function.

Thus far, practitioners have been unsuccessful in measuring fluorescence lifetimes with phase-based techniques and in using such measurements to identify the existence of particular analytes without complicated processing of the detected data signals. Indeed, where such signal processing is used to determine the lifetime of radiated cells within a flow cytometer, the performance of a selective sorting of such cells has been difficult since the processing may not be sufficiently rapid to enable sorting of the cells as they flow through the cytometer observation point.

In a system not previously used for flow cytometry, phase-modulation fluorometry and phase-sensitive fluorescence spectroscopy (PSFS) provide a means by which fluorescence lifetimes of one or a few fluorophores in homogeneous solutions are measured for the study of specific fluorophore lifetimes. One approach, described in PRINCIPLES OF FLUORESCENCE SPECTROSCOPY, J. R. Lakowicz, Plenum Press (1983), discloses a technique in which a sample containing only one or a few fluorophores is excited with light having a time-dependent intensity and a detection is made of the resulting time-dependent emission. Because the emission is demodulated and phase shifted to an extent determined by the fluorescence lifetime of the species, the fluorescence lifetime ($\tau$) can be calculated from the phase shift $\emptyset$ of the species:

$$\tau = \frac{1}{\omega} \tan \phi$$

or from a demodulation factor m:

$$\tau = \frac{1}{\omega} \left[ \frac{1}{m^2} - 1 \right]^{1/2}$$

where m is a demodulation factor, $\omega$ is the angular modulation frequency and $\emptyset$ is the phase shift of the species. Phase sensitive detection results from a comparison of the detected emission with an internal, electronic reference signal of the same frequency.

In a second approach, described in "Phase-Sensitive Fluorescence Spectroscopy: A New Method To Resolve Fluorescence Lifetimes Or Emission Spectra Of Components In A Mixture Of Fluorophores" Lakowicz et al, *Journal of Biochemical and Biophysical Methods;* vol. 5, 1981, pp. 19–35, the time-dependent fluorescence photodetector output signal is multiplied by a periodic square-wave signal which has the same modulation frequency as the fluorescence signal, and is then integrated. A time-independent dc signal is thereby produced that is proportional to the cosine of the difference between the phase angles of the square-wave and the fluorescence signal, and proportional to both signal amplitudes.

The two approaches described above are related to periodically modulated fluorescence excitation light. Consequently, continuous output signals are generated in both techniques. Therefore, these standard techniques would not have been considered to be used to measure fluorescence lifetimes of single cells passing the observation region in a flow cytometer. Moreover, as already mentioned, the output signal in the second technique depends not only on the fluorescence lifetime but also on the fluorescence signal intensity. As a matter of experience, the fluorescence signal intensity observed in a flow cytometer varies significantly from cell to cell, and therefore phase-modulation fluorometry and PSFS would not have been considered to be useful for flow cytometric measurements. Also, known phase modulation fluorometry methods use slowly responding circuits which would be expected to prevent cell-to-cell measurements.

SUMMARY OF THE INVENTION

According to the present invention, there is provided an apparatus and method for determining, in a flow cytometric environment, values corresponding to lifetimes of fluorescence emitted by single cells or particles associated with one or more fluorophores, in response to the illumination of the cells by modulated light of a wavelength corresponding to the excitation wavelength of the fluorophore.

Such a method of the present invention comprises directing a stream of individual cells past an observation point, irradiating each cell in the stream of cells with light modulated by an input signal at a preset frequency, and detecting the fluorescence emission of the fluorophore to produce a corresponding emission signal. There is generated an output signal which represents the change in phase and/or modulation between the input signal and the emission signal, which is indicative of the fluorescence lifetime of the fluorophore, and which is independent of the intensity of emitted light from the excited fluorophore.

One object of the present invention is to provide a method and an apparatus which increase the measurement, resolution, analysis and sorting capabilities of flow cytometers.

Another object of the present invention is to perform fluorescence lifetime measurements on single cells using phase resolution based on the decay time measured by the phase angle which is independent of the intensity of the emitted fluoresence.

Another object of the present invention is to implement a fluorescence lifetime measurement system which has an accurate and rapid response and is not dependent upon the intensity of the measured fluorescence.

Another object of the present invention is to implement a phase angle or modulation based fluorescence lifetime measurement system for application to a flow cytometer, which is simple, low cost and requires no counting circuitry.

In one embodiment, the detecting step is performed by means of a PMT, and the output signal is generated as a ratio of the the split PMT signals. The PMT signal is split, one of the signals is phase shifted 90°, and the two signals are ratioed to create an intensity-independent amplitude which reveals the phase angle. In another embodiment the PMT signal is mixed with a variable-phase input signal, and the mixer output is integrated and used to control the input signal to provide to the integrator a voltage output that corresponds to the phase shift of the emission signal relative to the phase of the input signal.

In another embodiment, in the irradiating step, the light source is a sync-pumped and cavity-dumped dye laser which is intensity modulated by a mode-locked signal, corresponding to the input signal, via a frequency synthesizer. According to another aspect of the present invention, a flow cytometer is provided that is operative to measure a fluorescence lifetime of at least one fluorophore associated with a cell or a particle, comprising: a flow chamber for directing a plurality of the cells or particles past an observation point; a modulated light source for irradiating, at the observation point, each cell or particle with modulated light at a frequency of an input signal and having a wavelength capable of exciting the fluorophore to produce an emission; a photodetector for detecting the emission and producing a corresponding emission signal; and a phase/modulation detector for generating an output signal corresponding to a change in phase and/or modulation between the emission signal and the input signal, wherein the output signal is indicative of the fluorescence lifetime of the fluorophore and is independent of fluorescence intensity.

In one embodiment, the photodetector is a PMT, and the apparatus further comprises a mixer and an integrator for mixing and integrating the output signal and the input signal to produce the voltage signal. In another embodiment, the integrator produces a signal having a constant voltage, wherein the voltage corresponds to the phase shift of the modulated fluorescence radiation.

In another embodiment, the light source is a sync-pumped and cavity-dumped dye laser which is intensity modulated by a mode-locked signal, corresponding to the input signal, via a frequency synthesizer.

According to another aspect of the present invention, there also is provided an apparatus for determining the lifetime of at least one fluorophore that is associated with a cell or particle in a flow cytometer, comprising a source of high intensity light at a selected wavelength capable of exciting the at least one fluorophore and modulated by an input signal at a set frequency, the modulated light being directed onto individual cells or particles, associated with the at least one fluorophore, passing an observation point in the flow cytometer to excite the fluorophore, a detector for detecting the emission from the excited fluorophore at the observation point to generate an emission signal, circuitry for splitting the modulating input signal into first and second signals that are in phase quadrature and for splitting the emission signal into third and fourth signals, circuits for mixing each of the first and second modulating signals with a respective one of the third and fourth emission signals, and ratio circuitry for creating the ratio of each of the two pairs of mixed signals to provide a lifetime signal which corresponds to the lifetime of the at least one fluorophore, such that the lifetime measurement is independent of the intensity of the fluorescence emission from the excited fluorophore.

DESCRIPTION OF THE PREFERRED EMBODIMENT

Figure 1:
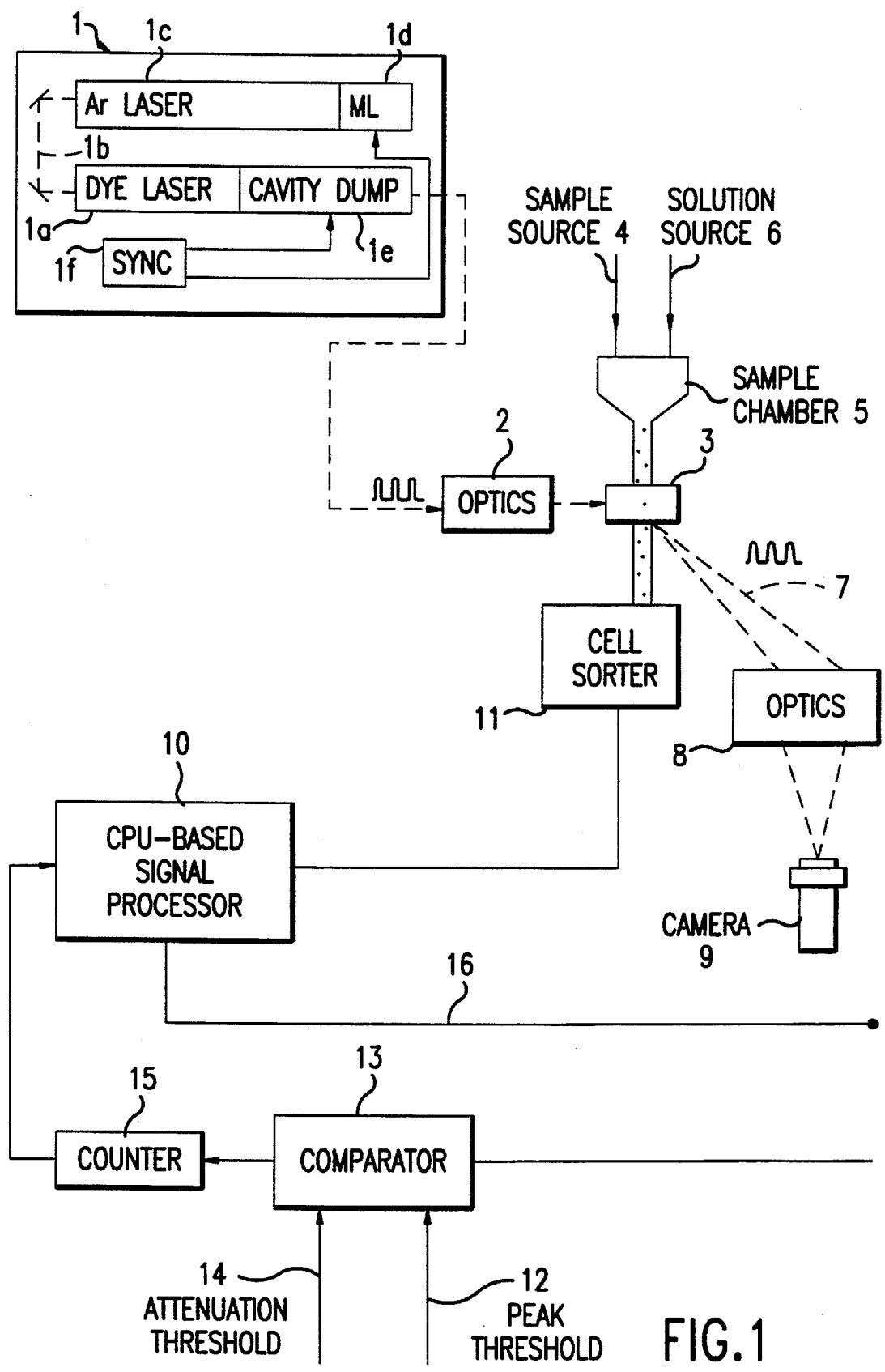
FIG. 1 is a block diagram of a conventional flow cytometric system which can detect fluorescence lifetimes.

The method and apparatus of the present invention will now be described in detail with reference to the accompanying drawing figures.

In contrast to the flow cytometry using intensity and/or wavelength based fluorescence detection, the present invention was discovered to unexpectedly provide apparatus and methods for characterizing and/or distinguishing cells or particles based on an average variation in the lifetimes of most or substantially all of the fluorophore molecules associated with cells or particles in a sample, which variation is directly due to the presence of an analyte in the cell or particle. Such variations have now been discovered to be dependent on the amount, concentration, or physical or chemical state of the fluorophore being sensed, such that practicable and commercially useful cell or particle characterization or distinguishing methods and apparatus can be provided according to the present invention.

Accordingly, analyte sensing can be achieved by methods of the present invention in which fluorophores, having emissions with a known lifetime when stimulated by light at a predetermined wavelength, are excited by a light source, such as a high frequency light source.

In the context of the present invention, the term "sample", which contains cells or particles to be used in flow cytometry according to the present invention, refers to compounds, mixtures, surfaces, solutions, emulsions, suspensions, mixtures, cell cultures, fermentation cultures, cells, tissues, secretions and/or derivatives or extracts thereof. Samples, as defined above, which can be used in methods of the present invention for sensing analytes based on fluorescence lifetimes also include samples that can be clear or turbid. Such samples to be measured according to the present invention require only that the fluorophore used be contacted with the sample such that the analyte to be sensed influences the lifetime of the fluorophore such that the lifetime varies with the presence or amount of the fluorophore.

Such samples can also include, e.g., animal tissues, such as blood, lymph, cerebral spinal fluid (CNS), bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ.

Additionally, samples that can be used in methods of the present invention include cell culture and fermentation media used for growth of prokaryotic or eukaryotic cells and/or tissues, such as bacteria, yeast, mammalian cells and insect cells.

The term "analyte" in the context of the present invention refers to elements, ions, compounds, or salts, dissociation products, polymers, aggregates or derivatives thereof.

Figure 2:
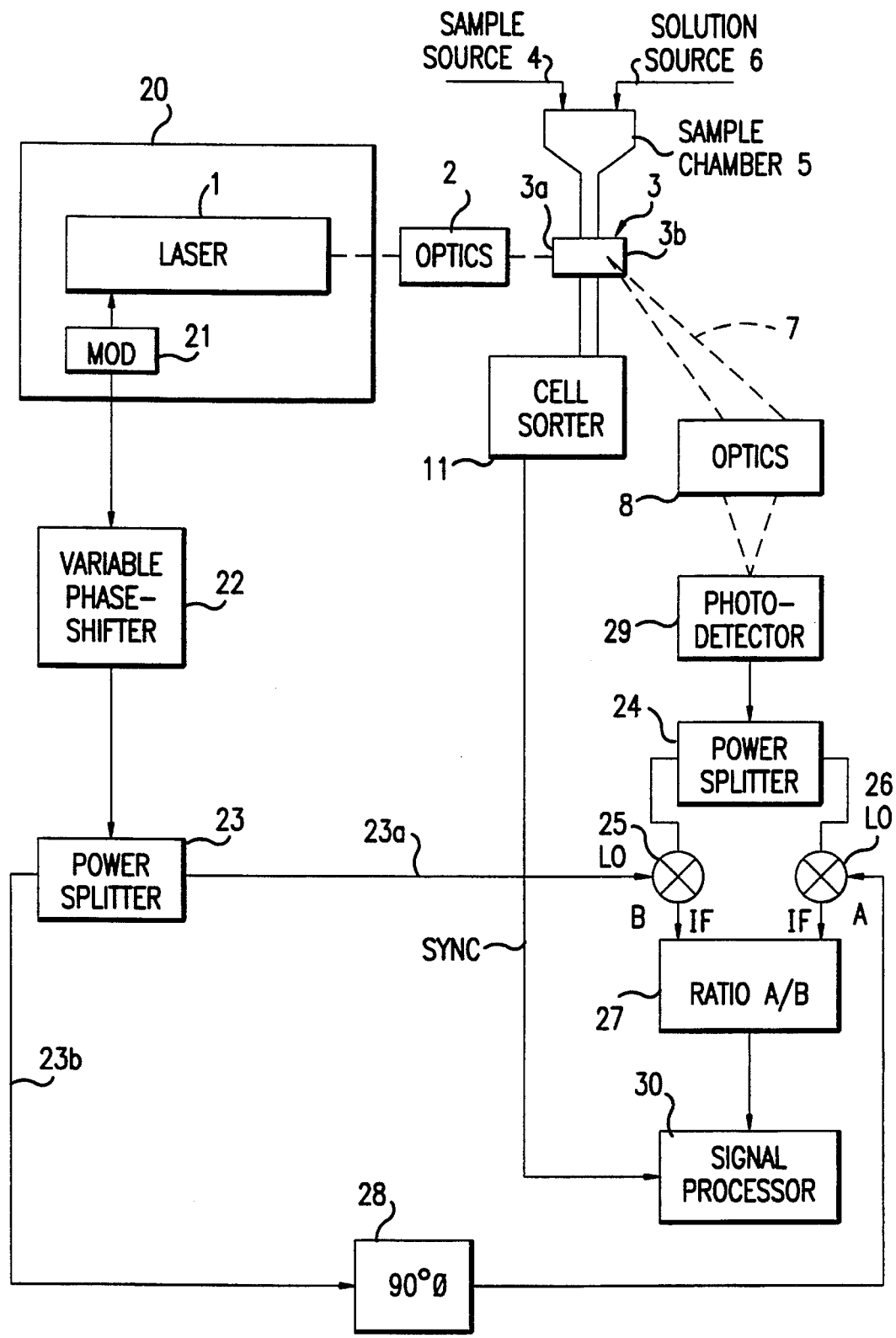
FIG. 2 is an illustration of a first embodiment of the present invention.

FIG. 2 is a block diagram of the overall configuration of an apparatus for phase-angle detection of the fluorescence lifetime of a cell or particle sample in a flow cytometer. Elements from the conventional flow cytometer system of FIG. 1 are identified by the same reference numbers within the flow cytometric environment of FIG. 2. Cell samples would be dyed with a suitable fluorescent dye having a known absorption characteristic for light within a particular wavelength and emitting light at a particular wavelength. Examples of such dyes are given in Table 1.

TABLE 1

| Dye Type | Laser Utilized for Dye Excitation | Dye Excitation/ Absorption Wavelength | Dye Emission Wavelength |
|---|---|---|---|
| DNA-staining dyes Hoechst 33342/ DAPI | Argon, Helium- Cadmium | 325–355 nm (UV) | 450 nm (blue) |
| Mithramycin | Argon | 457 nm (blue-violet) | 575 nm (green) |
| Chromomycin | Argon | 457 nm (blue-violet) | 555 nm (green) |
| Propidium iodide | Argon | 342–514 nm (UV to yellow) | 615 nm (orange-red) |
| RNA-staining dyes Pyronin Y | Argon | 480–550 nm (blue-green) | 570–600 nm (orange-red) |
| Protein-staining dyes Fluorescein | Argon | 488 nm (blue-green) | 520 nm (green) |
| Phycoerythrin | Argon | 488 nm (blue-green) peak 565 nm) | 578 nm (orange-red) |
| Texas Red | Krypton | 590 nm (green-orange) | 615 nm (orange-red) |

TABLE 1-continued

| Dye Type | Laser Utilized for Dye Excitation | Dye Excitation/ Absorption Wavelength | Dye Emission Wavelength |
|---|---|---|---|
| Allophycocyanin | Krypton/ Helium-Neon | 635–650 nm (red) | 670 nm (deep red) |

Many other compounds display changes in fluorescent lifetime in response to a variety of environmental parameters such as temperature, DNA composition, the presence or concentration of elements such as oxygen, sodium ions, calcium ions, potassium ions, magnesium ions and the existence of certain pH levels. For example, calcium ions in a cell or particle could be measured according to the present invention using an Argon laser and the flourophore Calcium Green. As would be clear to one of ordinary skill, currently known analytes, and those which may be developed in the future, having a known sensitivity to light at a particular wavelength, may be used.

Fluorophores suitable for use in methods or apparatus according to the present invention include fluorophores whose lifetimes vary directly with a concentration or amount of a particular analyte, as described herein, and which lifetimes are detectable by known fluorescence spectroscopy methods.

Accordingly, analyte sensitive fluorophores suitable for use in methods of the present invention include fluorophores that have fluorescent lifetimes which vary continuously over a suitable range of analyte concentrations or amounts, and are excitable with a suitable chromatic light, such as a laser light at a corresponding wavelength. Thus, the present invention provides for flow cytometry including the use of all fluorophores meeting the above criteria. These criteria can be determined by routine experimentation using known procedures which will be apparent to one of ordinary skill in the art. Therefore, fluorophores suitable for use in methods and apparatus of the present invention are not limited to the types and examples described herein, and are now discovered to correspond to those fluorophores which can be used for wavelength and intensity measurements. Fluorphores suitable for use in apparatus or methods of the present invention are available, e.g., from Molecular Probes, Inc., Junction City, Oreg.

In operation, as shown in FIG. 2, samples having a dye representative of the analyte to be detected are present in solution and are directed from the sample source 4 into the sample chamber 5. The sheath fluid from source 6 aligns the cells and causes them to pass in a stream, one cell at a time, past an observation point in the flow chamber 3 of the flow cytometer, in a manner well known in the art. At the observation point each cell in the stream of cells is irradiated, and the resulting radiation emission from each cell is detected. After passing through the observation point, the stream of cells may be formed into uniform droplets and sorted by a cell sorter 11, if desired. In accordance with the present invention, as further described herein, the sorting may be accomplished on the basis of detected fluorescence emission signals or the derived lifetime values for each cell.

Light source 20 is a periodically pulsed laser, whose output is directed to the source projection port 3a of flow chamber 3 via an excitation optics subsystem 2. In its preferred form, the light source is a mode-locked laser which is capable of generating pulses of light, exhibiting a broad spectrum of wavelengths in the ultraviolet range, at a fast repetition rate. The mode-locked laser is self triggering and requires no external timing, yet it can produce pulses at a repetition frequency in the Mhz-range which is sufficient to illuminate each cell with a pulse of light at least one time as it passes through the observation point of flow chamber 3. A preferred light source would comprise an argon laser, an internal modulated helium-Neon (HeNe) laser or a frequency-doubled YAG laser having a mechanism for generating light pulses by mode locking, a frequency-doubled dye laser for performing a wavelength conversion which permits the laser wavelength to match the sensitivity of the probe, and a cavity dumper for controlling the generation of light pulses at a desired rate and width. An appropriate pulse rate for the preferred embodiment would be $\geq 4$ MHz. Yet another light source structure may be found in the flow cytometer manufactured by Becton Dickinson Corporation, and sold under the trademark FACScan, where an air-cooled low-power 15 mW argon-ion laser operating at 488 nm, is used. The continuous light generated by the argon-ion laser would be externally modulated by an acousto-optical or electro-optical modulator to produce the desired pulsed or sinusoidal output, as will be explained in greater detail herein.

Light sources suitable for use in the methods of the present invention, also include noble gas light sources such as neon and argon and combinations, thereof. Light sources can include gas lamps or lasers which provide uniform light that has been filtered, polarized, or provided as a laser source, such as a coherent wave (CW) laser or a diode laser, e.g., a pulsed dye laser. Specified impurities can be added to the above described noble gas light sources to provide suitable light sources for use in the present invention with varying wavelengths such as emission and excitation wavelengths. Such impurities include Group II metals, such as zinc and cadmium. For example, a green helium neon laser as the light source for measuring fluorescent lifetimes according to methods of the present invention.

The light source can be modulated by the optic modulator as an acousto-optic modulator or an electro-optic modulator. Alternatively, the laser can be a periodically pulsed dye laser producing a laser pulse repetition frequency.

The beam emitted by the periodically pulsed laser 20 may be appropriately shaped by an excitation optics subsystem 2. For example, the Becton Dickinson FACscan cytometer employs a prismatic expander and spherical lens to provide an elliptical beam input to the source projection port 3a of a flow chamber. As each of one or more fluorophores that are associated with a cell or particle passes through the observation point in the flow chamber, the fluorophore will be excited by one or more pulses of light. A fluorescence emission of the fluorophore associated with the cell or particle as a result of illumination by the laser beam will result when the wavelength of the laser light matches the absorption band of one or more fluorophores used. The fluorescence emission will be at a longer wavelength and will have a delay time that characteristically identifies the fluorescent species, and can be modified by the presence of an analyte in or associated with the cell or particle.

In the present invention, such a fluorescence emission is received by an emission optics subsystem 8 which is designed to collect, direct and focus the light emitted at the flow chamber observation port 3b, as the sample passes through the observation point. Typically, such emission optics comprise an emission lens coupled to the flow chamber observation port 3b with the refractive indices matched by an optical gel. The light collection system may comprise a plurality of dichroic mirrors, which pass light at predetermined wavelengths and reflect light at other wavelengths. The optical system may use filters to separate the emitted light into its primary colors, and direct each monochromatic light beam into a separate channel for detection and analysis. In the preferred embodiment, plural channels are contemplated; however, for ease of illustration, only a single channel is shown in FIG. 2. It should be understood by one of ordinary skill that a plurality of channels, one for each respective monochromatic beam of light, would be employed. The emitted light at each color would be detected by an optical transducer, such as a photodetector 29.

The photodetector 29 is a sensitive, high speed device such as a Model R2496 or R928, manufactured by Hamamatsu Photonics K.K. The photodetector generates an output having a duration and amplitude which depends upon the duration and intensity of the received light beam at the wavelength to which the photodetector is sensitive. The photodetector produces a pulsed current output voltage which, in conventional flow cytometry systems, are directed to a signal processing subsystem for fluorescence analysis.

In accordance with the present invention, however, the laser light source 20 is itself subject to pulse or sine wave amplitude modulation. This modulation may be internally generated for a mode-locked laser or may be externally generated by a trigger circuit, as in the case of a cavity dumped laser, or a local frequency generator generating a sine wave at a desired modulation frequency. The schematic illustration of FIG. 2 illustrates a separate modulator driver 21, but is intended to represent an internally generated modulation as well. This unit provides from the laser a sinusoidal output. In the preferred embodiment, the modulating frequency would be within the GHz to MHz-range, e.g., at 80 MHz. The laser modulator may be a TEM-20-7.5 Model modulator manufactured by Brimrose Corp. of America, and having an auxiliary synchronization output. When the laser is mode-locked and generates the modulation internally, the modulation frequency can be detected at a point on the laser. The exciting laser beam, whether mode-locked internally or modulated externally, has a periodically varying intensity.

Figure 3:
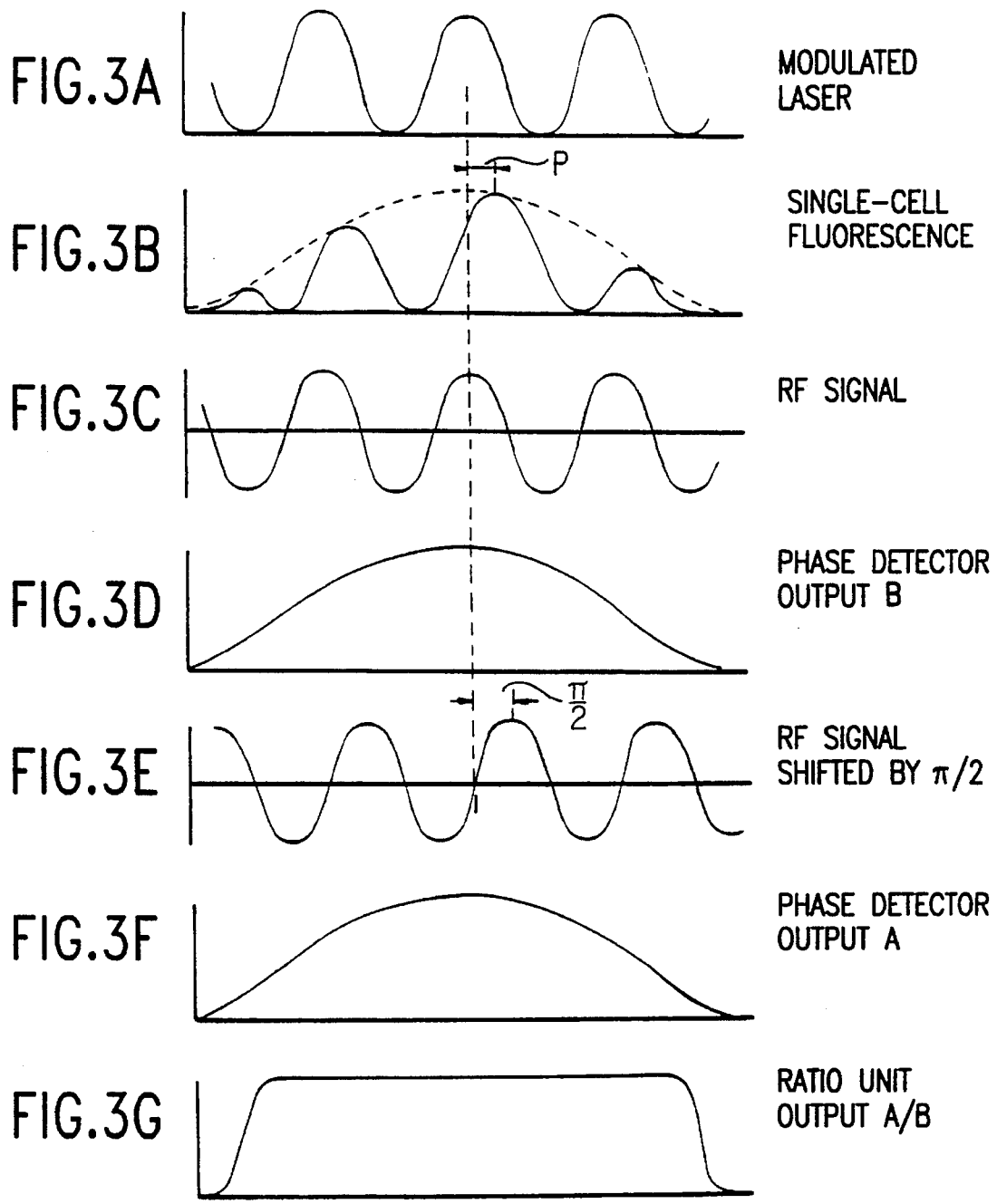
FIGS. 3A–3G show waveforms of signals in the embodiment shown in FIG. 2.

The intensity of the fluorescence emitted by the excited probe material is directly dependent on the intensity of the excitation beam. Thus, the fluorescence emission will be modulated at the same frequency as the exciting beam. In the preferred embodiment, since the exciting beam is modulated at a 80 MHz frequency, the fluorescence response will exhibit an intensity which also varies at a 80 MHz frequency. Recognizing that a graphical representation of the pulsed fluorescence signals will be for illustration only, a representation of a sinusoidal excitation output intensity $I_1$ from the laser 1 unit is seen in the waveform illustrated in FIG. 3A. This waveform varies at a frequency f1 which is 80 MHz in the preferred embodiment. A representation of the intensity $I_2$ of the fluorescence emitted from the sample, following illumination by the modulated light source, is seen in FIG. 3B. From the waveform illustrated in that Figure, it is clear that the emission is modulated at the same frequency f1 as the exciting beam and has a sinusoidal characteristic but experiences a phase lag (P) relative to the exciting beam. The phase lag P results from the characteristic delay which is experienced by a fluorophore in emitting its fluorescence after excitation. The phase lag P is seen by a comparison of the waveforms illustrated in FIGS. 3A and 3B. It has been determined that the phase lag P is related to the fluorescence lifetime $\tau$ in accordance with the following equation:

$$\tan(P) = 2\pi f \tau,$$

where f=the modulation frequency.

The structure of the invention as illustrated in FIG. 2 is intended to utilize this relationship and to provide an output signal with an amplitude that is proportional or otherwise related to the fluorescence lifetime. This relationship may be established empirically, or the relationship may be understood from the known nature of intensity decay and the phase and/or modulation detection circuits. Referring again to FIG. 2, the output from the modulator driver 21 and the output detected by the photodetector 29 are processed in order to derive an intensity-independent signal which is indicative of fluorescence lifetime. An output is taken from the auxiliary terminal of modulator driver 21 (or directly from a terminal of a mode-locked laser) and is directed via variable phase shifter 22 to a two-way 0° power splitter 23. The signal output of the photodetector 29 also is connected to the input of a two-way 0° power splitter 24. Each of the two power splitters can divide the power of the input signal in a specified proportion between each of its respective two output ports, without affecting the frequency and phase of the input signal. In the preferred embodiment, the power division is equal; each output of power splitter 23 is one-half of the power input from variable phase shifter 22 and retains the same modulation frequency and phase of the signal generated at the output of the modulator driver 21. In this first embodiment, variable phase shifter 22 is assumed to provide no phase shift in the output from modulator driver 21; however, as disclosed subsequently, a specified shift may take place in order to suppress the unwanted signals of auto fluorescence and/or stray light.

Each of the two RF outputs from power splitter 24 also receives one-half of the power of the output signal from photodetector 29 and maintains the frequency and phase of that output signal. Thus, the two RF outputs from power splitter 24 have a 80 MHz frequency and have a delayed phase relationship with respect to the RF outputs of the power splitter 23.

The two outputs of power splitter 24 are connected to the RF inputs of a first phase detector 25 and a second phase detector 26. The waveforms of these signals correspond to the fluorescence waveforms shown in FIG. 3B. These two phase detectors are RF mixers with a low DC offset and with a high figure-of-merit, measured in maximum DC output voltage in mV divided by the RF input power in dBm. The respective outputs of each of the first phase detector 25 and second phase detector 26 are provided to a ratio unit 27 which generates an output signal corresponding to the ratio of the output signals of the phase detectors 26 and 25. Such ratio unit may be a Model AD 539 manufactured by Analog Devices.

A second input signal to the first phase detector 25 is provided by one output 23a of power splitter 23. This RF signal is shown in FIG. 3C. As previously noted, the first phase detector 25 is an RF mixer which receives the output 23a of the power splitter 23 at its LO input and produces a first input B to the ratio detector 27. The signal B is shown in FIG. 3D. In operation, the output of the phase detector 25 is an IF signal that is proportional to $I \cos D$, where I is the fluorescence intensity and D is the phase difference between the photodetector RF signal and the synchronization output LO signal.

The other output 23b of power splitter 23 is connected via a fixed 90-degree phase shifter 28 to the LO input of the second phase detector 26. The phase-shifted RF signal is shown in FIG. 3E. Due to the fixed 90-degree phase shift, the output IF signal A of the phase detector 26, illustrated in FIG. 3F, is proportional to $I \sin D$, where I and D have the same meaning previously discussed with respect to the output of phase detector 25.

The ratio unit 27 receives a signal $I \cos D$ and $I \sin D$ and generates an output signal R which corresponds to the ratio between the output signals of the phase detectors 26 and 25. Referring to the value of these output signals, the ratio unit output amplitude is represented by the following equation:

$$R=(I \sin D)/(I \cos D)=\tan D.$$

The amplitude of the output from the ratio unit 27 is independent of the fluorescence intensity I, as is indicated in FIG. 3G. For fluorescence radiation, the output intensity is $R=\tan D=2\pi.f.T$ where f is the LO frequency which is constant for a particular measurement, and $\tau$ is the fluorescence lifetime. The ratio unit output amplitude R, is thus directly related to the fluorescence lifetime $\tau$ and is independent of the fluorescence intensity I. In practice, the signal may not be precisely proportional to the lifetime but, in any event, will be sufficiently related to lifetime so as to enable discrimination among particles.

The output amplitude R may be detected and processed by conventional hardware and software 30, currently capable of processing the pulse amplitude output from existing flow cytometers. A computer can convert the output R into decay times and use such decay times for analysis and cell sorting. Thus, using existing fluorescent probes, it is possible to measure cellular pH, cations, oxygen concentration and $Na^+$ composition since fluorophores are known whose decay times are sensitive to these parameters. With the advent of this new technology, fluorophores will be developed whose decay times are sensitive to a variety of analytes and will allow enhanced study of cellular physiology on a cell-by-cell basis. For example, fluorescence lifetimes may depend on the concentration of particular analytes. Therefore, the measurement of such lifetimes can identify the presence of those analytes. Fluorescent compounds, which display changes in lifetimes in response to temperature, oxygen, pH, and the presence of particular elemental ions such as those of sodium and calcium, may be used.

The flow cytometer with phase fluorescence lifetime measurement ability, as seen in FIG. 2, also has an autofluorescence signal suppression capability. The light detection system may be adjusted electrically in such a way that the output signals of unwanted autofluorescence and/or non-rejected stray light become equal to zero. As seen in FIG. 2, the variable phase shifter 22, which receives the output of modulator driver 21 (or the detected output of a mode-locked laser) and provides that modulation signal to power splitter 23, may be set to provide a zero phase shift in a first embodiment. However, in a second embodiment, the signal contribution of unwanted autofluorescence can be suppressed if the variable phase shifter 22 is adjusted so that the phase difference for autofluorescence radiation at phase detector 26 is equal to zero. Alternatively, the phase of the LO input to 25 is adjusted to be 90° shifted from the input signal to 25. By reducing the autofluorescence signal to zero, fluorescence with a lifetime different from the autofluorescence lifetime can be easily detected. When A is the phase shift angle resulting from the autofluorescence lifetime $\tau_A$, the variable phase shifter 22 has to be adjusted to a shift angle equal to A. Under these conditions the output amplitude of the ratio device for autofluorescence present may be given by the expression:

$$R=[\sin (D-A)]/[\cos (D-A)]=\tan (D-A).$$

Thus, fluorescence with a lifetime T longer than $\tau_A$ generates positive output amplitudes, auto fluorescence with a lifetime $\tau=\tau_A$ generates no signal, and fluorescence with lifetimes $\tau$ less than $\tau_A$ generates negative amplitudes. As in the first embodiment, the amplitudes in this embodiment are independent of the fluorescence intensity and can easily be corrected by a computer in order to normalize the output signal to only positive values.

The signal-suppression capabilities of a flow cytometer according to the present invention are not limited to autofluorescence with a single-exponential decay. For an autofluorescence showing any kind of kinetics, there exists a specific phase setting of the variable phase shifter that causes the autofluorescence signal to become equal to zero. This principal is applicable also to a combination of autofluorescent light and unrejected scattered radiation. The only condition that must be fulfilled in this case is that the relative contributions of autofluorescence and scatter must remain constant.

Figure 6:
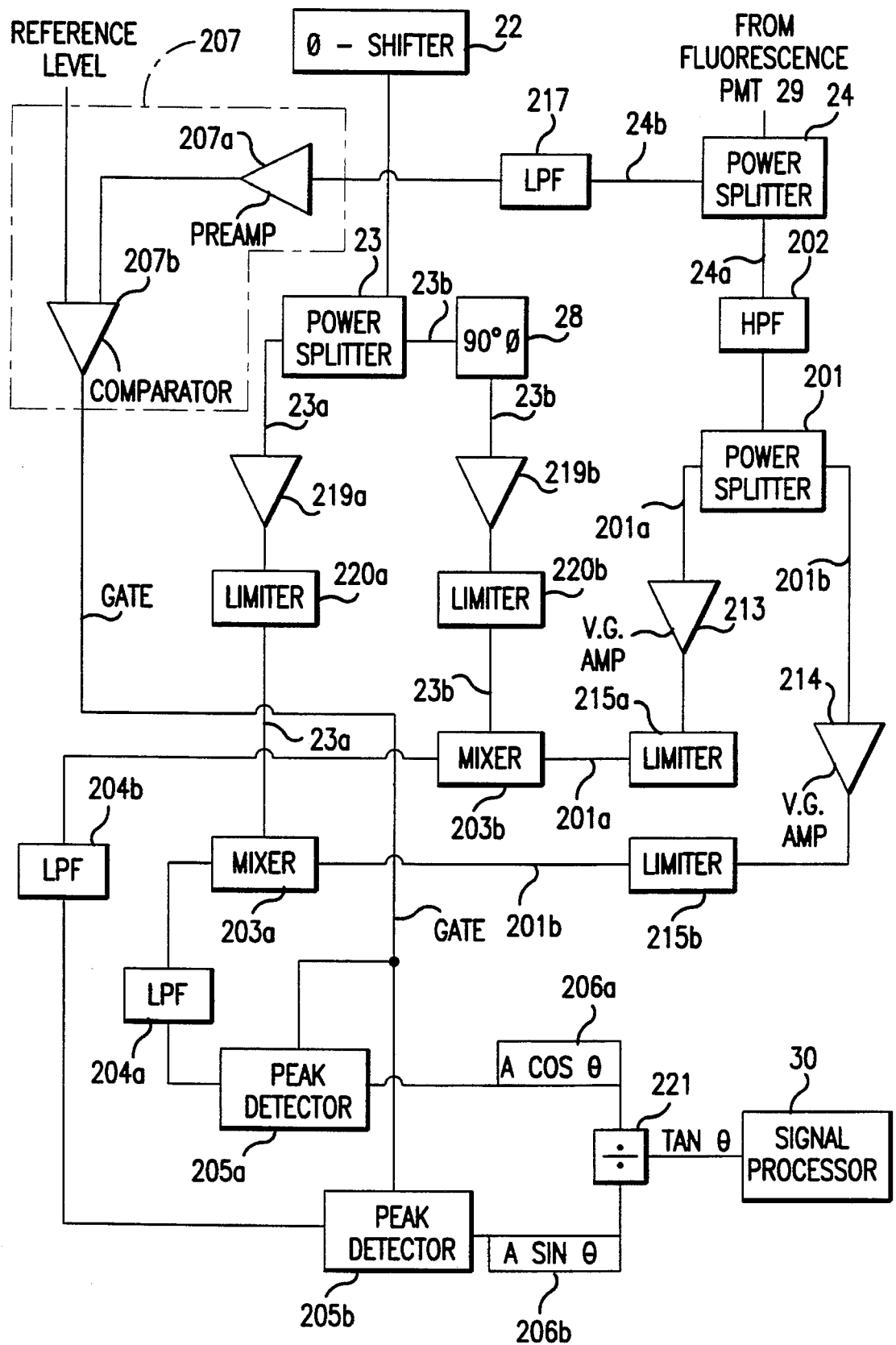
FIG. 6 is a schematic block diagram of a fourth embodiment of the present invention.

FIG. 6 shows a further embodiment of the present invention which allows for phase detection without intensity dependence and which involves modifications to the embodiment, as variations thereof, presented in FIG. 2.

In particular, in FIG. 6, the split output signal 24a of the power spitter 24 (FIG. 2) is fed via the high pass filter 202 to an additional non-phase shifting power splitter 201 which provides two split output signals 201a and 201b which are routed through respective limiters 215a and 215b after amplification in respective variable gain amplifiers 213 and 214. The modulating signal from the frequency generator 21 and the phase-shifter 22 shown in FIG. 2 is also split by a power splitter 23 in two equal output signals 23a and 23b.

The split output signal 23b is phased shifted by 90 degrees in a phase shifter 28, while the other split output signal 23a is kept in phase with the output of the frequency generator 21 (FIG. 2). The in-phase and phase-shifted signals are amplified by respective amplifiers 219a and 219b, limited by respective limiters 220a and 220b and fed to respective double balanced mixers 203a and 203b where they are mixed with the split and limited fluorescence output signals 201a and 201b, respectively. The resulting output signals of the mixers 203a and 203b are low pass filtered via low pass filters 204a and 204b and peak detected via peak detectors 205a and 205b, which are gated by the comparator circuit 207 to produce two output voltages 206a and 206b corresponding to cosine and sine, respectively of the emission signal of the detector PMT 29 of FIG. 2. The gating is accomplished via the comparator 207 which comprises a preamplifiers 207a and a comparator 207b whose output signal gates or enables the peak detectors only after the envelope of each peak has passed a predetermined threshold value, determined by a reference signal inputted by the comparator 207b as a predetermined threshold level corresponding to amplitude limits encompassing the amplified and limited fluorescence output of the detector PMT 29 (FIG. 2), and disables the detectors 205a and 205b when the signal envelope drops below the threshold. The ratio of the output voltages 206a and 206b is then determined by a modulation ratio unit 221 whose output is intensity independent, since the peak voltage is representative of the tangent of the phase and/or modulation change between the fluorescence output signal originating from the detector PMT 29 and the reference signal from the frequency generator 22 (FIGS. 2). This change in phase and/or modulation corresponds to the fluorescence lifetime of the fluorophore associated with the cell or particle passing through the flow cell chamber 3 (FIG. 2). To determine this change in phase and/or modulation, the output voltage from the modulation ratio unit 221 is fed into the signal processor 30.

Optionally, a limiting circuit can receive and limit the output signal produced by the photodetector. Limiting circuits are described, e.g., Spencer, thesis, University of Illinois at Urbana-Champaign, 1970. A preferred limiting circuit is model PLS-1 from Mini-Circuits, Brooklyn, N.J. The limiting amplifier results in phase angle measurements based on detection of zero crossing, which are mostly independent of signal amplitude. While the limiting circuit produces additional harmonics of the signal from the photodetector, the effect of the limiting circuit is to eliminate all signals above a preset level. The limiting circuit provides such a centroid signal which maintains the same phase characteristics of the output signal which the output signal had prior to comparison of the output signal with the input signal of the light source.

While some phase shifting of the signal can occur with the use of a limiting circuit, the harmonics and band noise produced by the limiting circuit can be removed by the use of one or more known low and high pass filters. Preferably, the output signal from the photodetector can be low and high pass filtered and amplified with an optional filter/amplifier, prior to limiting by the limiting circuit.

Figure 5A:
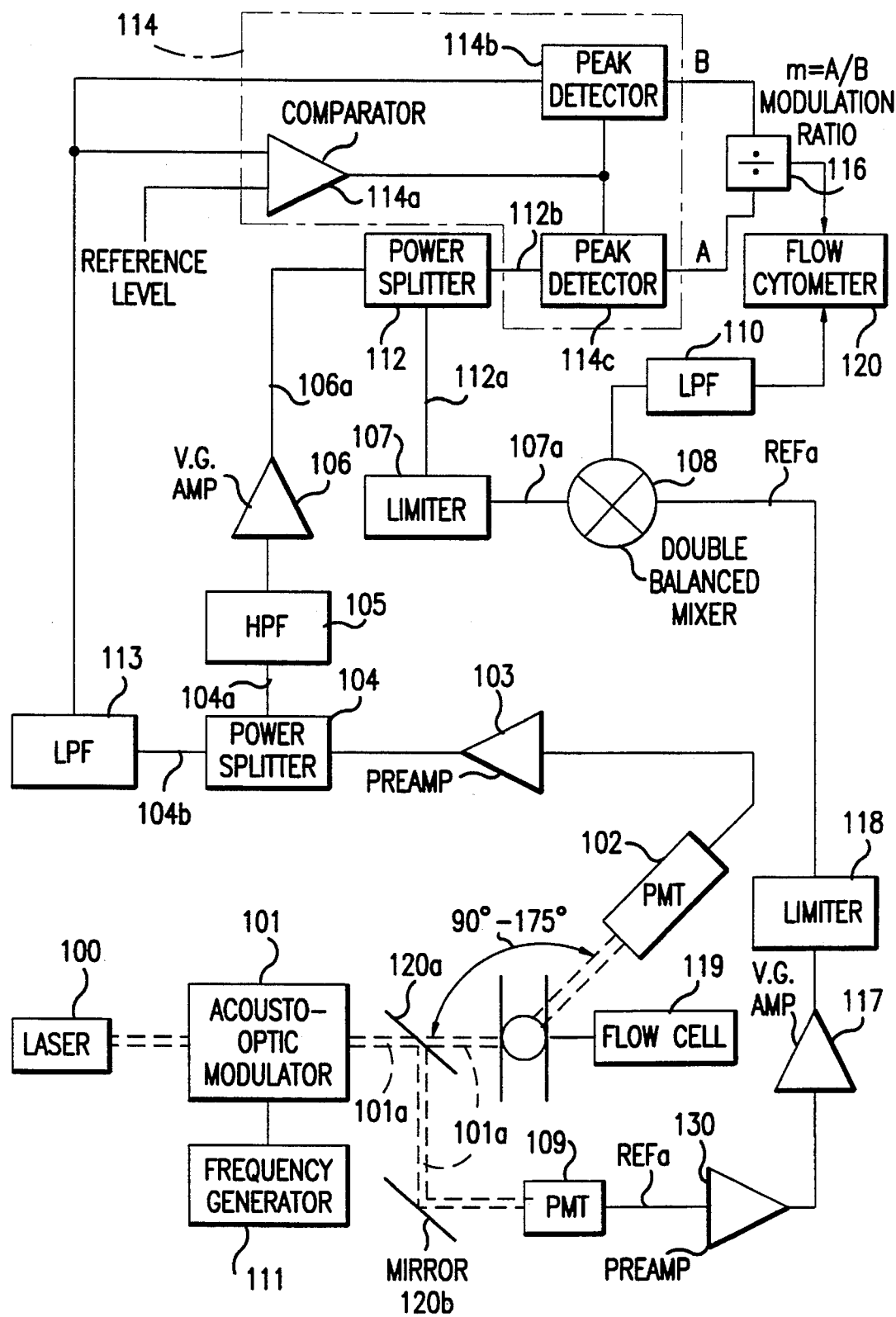
FIGS. 5A and 5B are schematic block diagrams of a third embodiment and a variation thereof, respectively.

Accordingly, an alternative embodiment of the present invention is shown in FIG. 5A. A laser source 100 produces a laser beam which is frequency modulated at a frequency of up to 100 MHz with an acoustic optic modulator 101 driven by a frequency generator 111 to produce a modulated laser light beam 101a. The modulated laser light beam 101a passes through a beam splitter 120a and illuminates a fluorophore-associated cell, bead or particle in a flow cell 119 to produce a fluorescence emission from the fluorophore. The resulting fluorescence emission is then detected by a detector 102 at a side scattered position of 90 to 175 degrees to the incident modulated laser beam 101a. The detector such as a PMT 102, detects the fluorescence emission and produces a corresponding electrical output signal.

The fluorescence electrical output signal, after 10 dB of amplification by a preamplifier 103, is split into two equal signals 104a and 104b, respectively, by a power splitter 104 while maintaining fidelity and relative amplitude without inducing additional intensity dependent phase shifts. A first signal 104a from the power splitter 104 is fed through a high pass filter 105 and then mixed and further amplified in a variable gain amplifier 106, whose output 106a is split by a power splitter 112 to provide a first split signal 112a which limited to a suitable operating range by a limiting circuit 107. The second split signal 112b is peak detected in a peak detector 114c forming part of a gated peak detector circuit 114.

The output 107a of the limiting circuit 107, as a limited signal which phase shifted relative to a reference signal (REFa or REFb, as presented below), is then mixed (e.g., multiplied) via a double balanced mixer 108 with the reference signal REFa or REFb obtained as follows:

(A) A reference signal REFa (FIG. 5A) is produced in the following manner. A detector, such as a PMT 109, detects the modulated laser light beam 101a which has been split by a beam splitter 120a and reflected by a mirror 120b. The detector PMT 109 then produces a corresponding output electrical signal which is amplified by 10 dB by a preamplifier 130, amplified by a variable gain amplifier 117 and then limited by a limiting circuit 118 to produce the reference signal REFa.

Figure 5B:
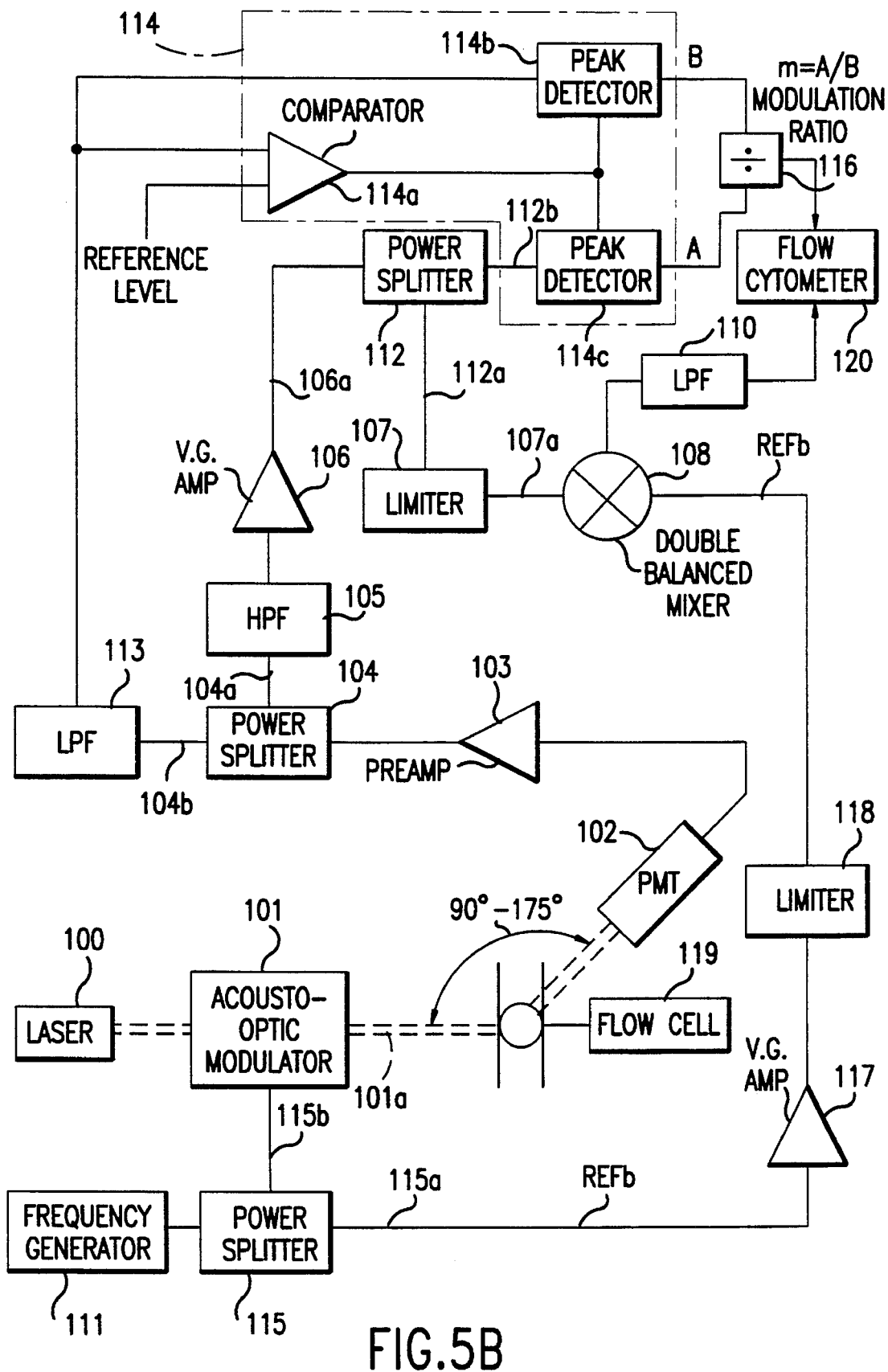

(B) A reference signal REFb (FIG. 5B) is produced in the following manner. The electrical output signal from the frequency generator 111 is split by a power splitter 115 into two signals 115a and 115b, respectively. The signal 115b drives the acousto-optic modulator 101. The signal 115a is amplified by a variable gain amplifier 117 and then limited by a limiting circuit 118 to produce the reference signal REFa.

The multiplied output signal of the mixer 108 is produced by the mixing of (1) the reference signal REFa or REFb from the limiter 118 and (2) the phase shifted limited signal 107a from the limiting circuit 107. The multiplied output signal from the mixer 108 is filtered via a low pass filter 110 and the peak voltage of the multiplied output signal is a measure of the relative phase shift of the output signal from the PMT 102 to the reference signal REFa or REFb originating from the frequency generator 111. The filtered multiplied output signal from the mixer 108 via the low pass filter 110 is detected via a peak and hold circuit in the flow cytometer 140. The fluorescent lifetime is related to the detected output signal as follows:

$$Vp = v + c * \cos(\text{phase})$$

where Vp=peak voltage c is proportional to pulse amplitude, v is an offset voltage unique to the limiter, and phase=arc cos ((Vp–v/c); and $T=(\tan(\text{phase})/2*\pi*f$, where $\pi=3.1416$, f is operating frequency and $\tau$ is the fluorescence lifetime.

The signal 104b obtained from the power splitter 104 is filtered by a low pass filter 113 to produce a low pass filtered signal detected via a gated peak detector circuit 114 comprising a comparator 114a and a peak detectors 114b and 114c. The amplitude of the low pass filtered signal is gated to the peak centroid via the comparator with a reference signal, inputted as a predetermined threshold level corresponding to amplitude limits encompassing the amplified and limited fluorescence output of the detector PMT 102, and a peak detector 114b to produce an output signal B. The high pass filtered signal, originating from the power splitter 104 as signal 104a, is gated via a peak detector 114c to produce a signal A. The gated high pass filtered signal A is then compared to the gated low pass filtered signal B and a modulation ratio is determined via a modulation ratio unit 116.

This modulation ratio is then inputted into the flow cytometer 120 and provides a measure of the relative depth of modulation "M" between the (1) the reference signal REFa or REFb from the limiter 118 and (2) the phase shifted limited signal 107a from the limiting circuit 107.

When the flow cytometer determines the lifetime of the fluorophore based on the modulation ratio, if the first order of the reference signal REFb (FIG. 5B) is used to determine the depth of modulation "M", then the modulation ratio will directly correspond to the depth of modulation and no correction factor will be needed. However, if the zeroth order of the reference signal REFb (FIG. 5B) is used to determine the depth of modulation "M" then the modulation ratio will not directly correspond to the depth of modulation and a correction factor of percent modulation of the reference signal will be necessary.

The ratio modulation outputted from the modulation ratio unit 116 and multiplied output signal from the mixer 108 via the low pass filter 110 are inputted into the flow cytometer 130 to provide the apparent fluorescent lifetime based on (1) the modulation ratio of the peak voltages from the peak detectors 114b and 114c and (2) change in phase of the detector 102 output signal, as compared to the reference signal REFa or REFb.

The resulting peak voltage is a measure of the apparent fluorescent lifetime by the following relationship.

$$t = (\text{square root of}((1/(M*M))^{-1})/(2*\pi*f)$$

where M=the ratio of the amplitudes.

Figure 4:
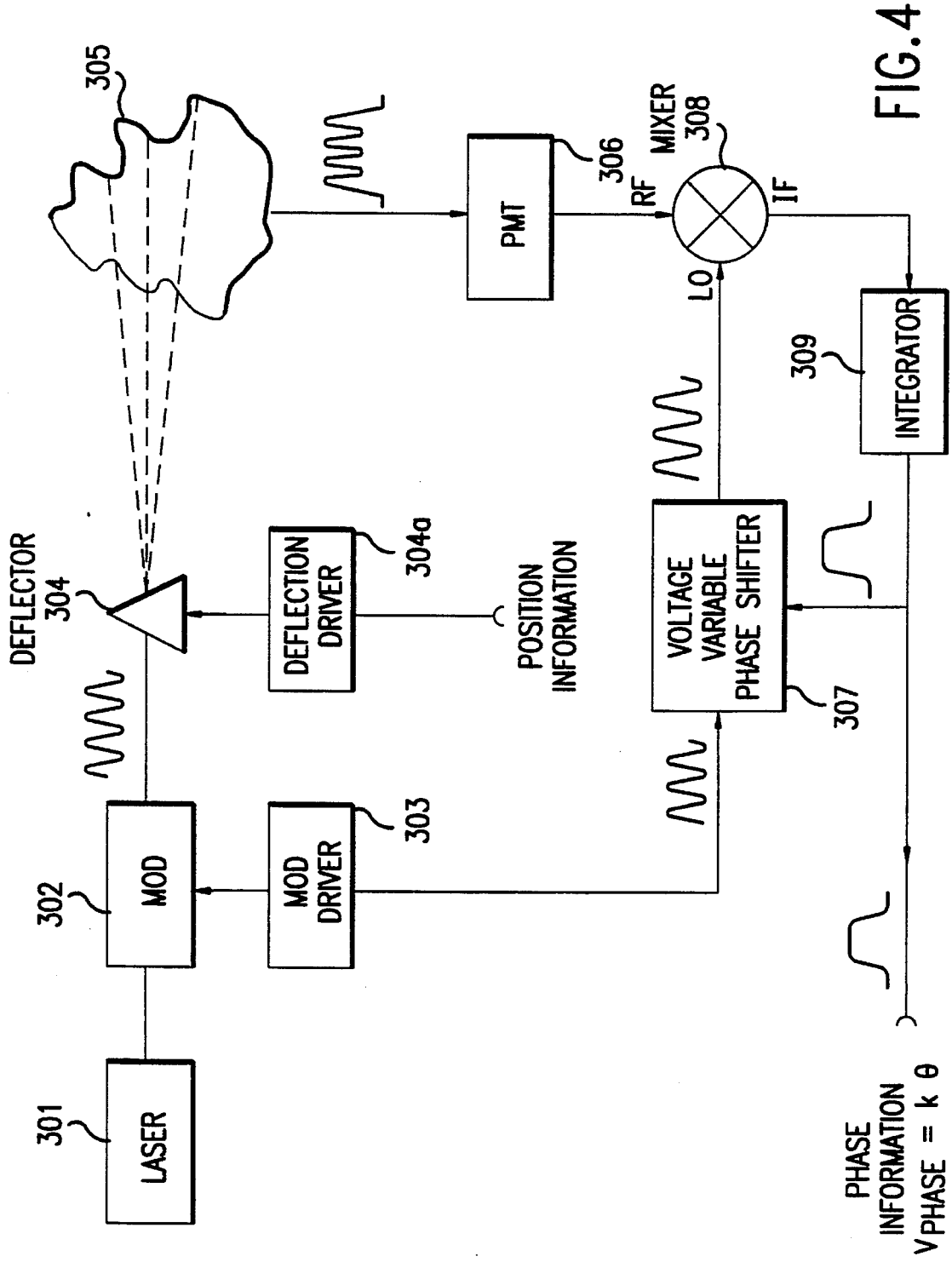
FIG. 4 is a schematic block diagram of a second embodiment of the present invention.

An alternative embodiment of an apparatus and method according to the present invention is shown schematically in FIG. 4. The output light of a laser 301 is intensity modulated by a optical modulator 302 driven by a sinusoidal modulation signal from an electrical modulation driver 303. The resulting intensity modulated laser light is deflected via a deflector 304 and a deflection driver 304(a) onto a sample 305 containing one or more analytes, particles or cells. A fluorescence photodetector, such as a PMT (photomultiplier tube) 306, detects the fluorescence emission and produces an electrical output signal which is fed to the RF input of a mixer 308. The sinusoidal modulation signal from the modulation driver 303 is also fed to the input of a voltage variable phase shifter 307 whose output is connected to the LO input of the mixer 308, and the IF output of the mixer 308 is fed to an integrator 309, whose output is fed to the voltage-control input of the variable phase shifter 307. The integrator output contains the phase change or modulation information, thereby providing the cell's change in lifetime due to the presence of the analyte, particle or cell associated with the fluorophore.

When the RF signal and the LO signal at the mixer are 90° out of phase, the IF output signal is equal to 0. When the fluorescence light is phase-shifted by an angle θ relative to the laser light source, the mixer IF output signal is different from 0. This IF signal is integrated, and the voltage of the integrated output signal is fed back to shift the LO signal phase the required amount to place the RF signal and the LO signal 90° out of phase at the mixer 308. When this condition is achieved, the IF output signal of the mixer 308 again becomes equal to 0, and the integrator 309 output voltage remains constant. Since this required LO signal phase shift is identical to the fluorescence phase shift angle θ, the phase-shifting control voltage contains the required phase information.

According to this operational principle, the LO signal phase is shifted until the IF signal is equal to 0, such that the phase detector output is independent of the fluorescence pulse amplitude. Because the voltage controlled phase shifters have much shorter response times than dividers, as presented above and as shown in FIG. 2, the present embodiment of the invention (as shown schematically in FIG. 4) can provide faster phase measurements than are obtainable by a divider-based phase detector. Additionally, this embodiment provides more stable phase information because no divider is required, whereby the phase shift is indicative of a fluorescence lifetime of a dye corresponding to a physical or chemical change in a condition of an analyte, cell or particle.

Other objects, features and advantages of the present invention will become apparent to those skilled in the art from the above detailed description and following Examples of the present invention. It should be understood, however, that the description and specific examples, while indicating preferred embodiments of the present invention, are given by way of illustration and not limitation. Many changes and modifications within the scope of the present .invention may be de without departing from the spirit thereof, and the present invention includes all such modifications.

EXAMPLE 1

Lifetime Based Flow Cytometry

The following example utilizes an embodiment of the present invention as described above and in FIGS. 5A and 5B and FIG. 6.

Figure 7A:
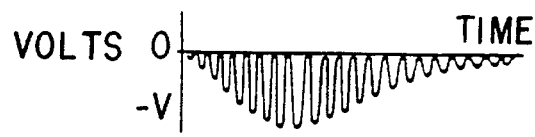
FIGS. 7A–7F are graphical representations of waveforms produced in phase fluorescence lifetime measurements.
Figure 7B:
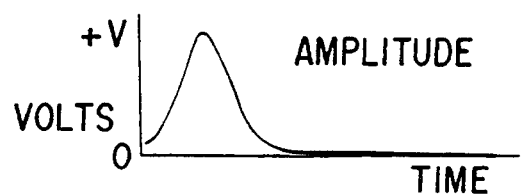
Figure 7C:
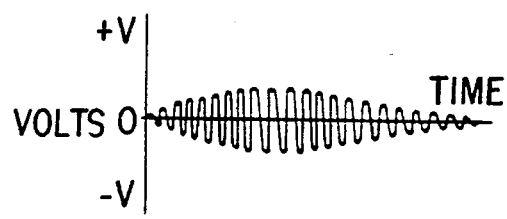

FIGS. 7A–7F illustrate the phase fluorescence lifetime measurement with pulses from 2 micrometer diameter fluorophore dyed particles as Fluoresbrite™ particles (available from Polysciences, Inc., Warrington, Pa.) analyzed on a computerized flow cytometer, such as the FACStar™ (also available Becton Dickinson Immunocytometry Systems). FIG. 7A shows the signal from the fluorescence detector, such as a PMT which signal is a 20 MHz signal modulated by the signal amplitude. If the signal in FIG. 7A is put through a low pass filter to remove the 20 MHz component, the result is the standard fluorescence amplitude signal, FIG. 7B, which amplitude is normally detected in a flow cytometer. If the signal in FIG. 7A is fed through a high pass filter the result is shown in FIG. 7B, which signal can be further analyzed for phase shift relative to a reference signal used to modulate the laser light source, such that the phase shift corresponds to the fluorescent lifetime of the fluorophore associated with the cell or particle in the flow chamber.

Figure 7D:
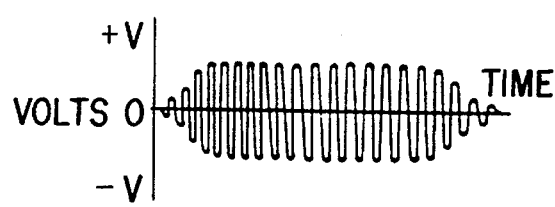

Before analyzing for the phase shift and or modulation, the signal is fed through a limiter which provides a flat-topped signal during the peak of the signal, as shown in FIG. 7D. The flat-topped region or voltage level of FIG. 7D provides a phase measurement that is relatively independent of the amplitude of the unlimited raw signal in FIG. 7A.

Figure 7E:
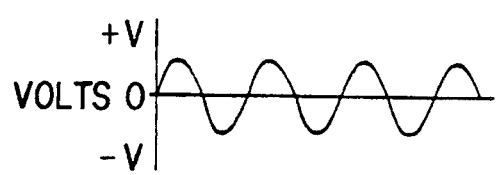

To measure the phase shift of the detector output signal relative to the reference signal, the limited signal from FIG. 7D is mixed with the reference signal in FIG. 7E. The reference signal in FIG. 7E is also used to modulate the laser beam. If there is little or no phase shift, such a short fluorescence lifetime will provide a limited signal (FIGS. 7A, 7C and 7D) that is almost exactly in phase with the reference signal, FIG. 7E, e.g., where the fluorophore used is provided in Fluoresbrite™ particles.

Figure 7F:
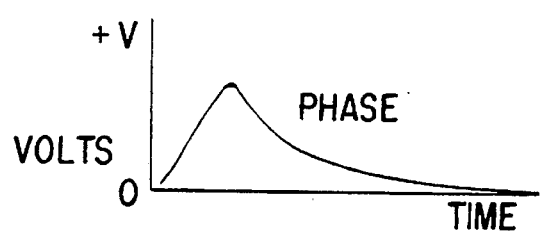

The output of the phase-detector, e.g., can be proportional to cos(p), where p is the phase angle. If p=0, there is no phase shift since the fluorescent lifetime zero or is so short as to not be detectable, and the output of the phase detector is maximal, cos(0)=1. As the lifetime increases, the phase angle increases, and the output voltage of the phase detector decreases. Longer lifetimes produce phase detector output signals of smaller amplitude. Phase detector output signals for the Fluoresbrite™ particles are shown in FIG. 7F. By use of a second mixer, a 90° phase shift, and a ratio circuit, these signals can be used to determine the phase angle.

To determine the phase detector response as a function of the fluorescence signal amplitude, particles were run on a FACStar™ flow cytometer and the PMT voltage was varied while data was being taken. For an ideal phase detector, the phase output would be independent of the fluorescence intensity.

Figure 8:
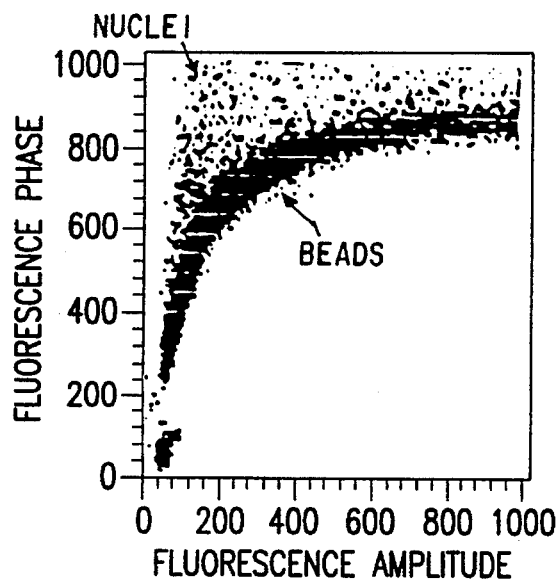
FIG. 8 is a graphical representation of phase fluorescence versus fluorescence amplitude of cell nuclei stained with ethidium bromide and fluorophore dyed particles.
Figure 9:
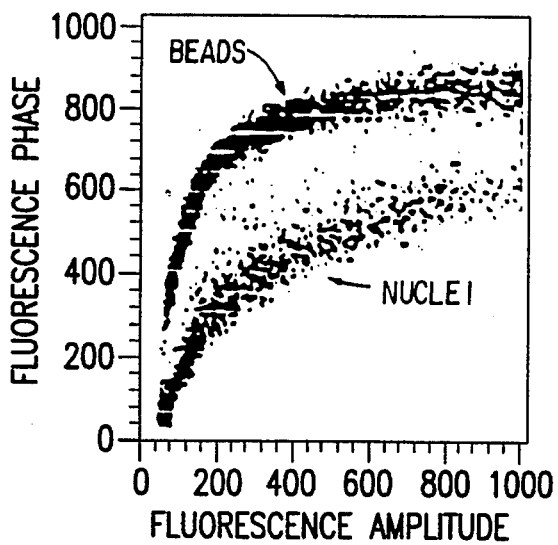
FIG. 9 is a graphical representation of phase fluorescence versus fluorescence amplitude of cell nuclei stained with ethidium bromide and fluorophore dyed particles with the use of an optical band pass filter.

FIGS. 8 and 9 show results wherein samples contained a mixture of 2 micrometer Fluoresbrite™ particles and calf thymocyte nuclei stained with ethidium bromide (EB). DNA stained with EB is reported to have a fluorescence lifetime of 24 ns. The x-axis is the standard fluorescence signal amplitude, while the Y-axis is the output of the phase detector. In FIG. 8, the filter used for the PMT passed only laser light scattered by the sample particles having no phase lag and thus maximum phase detector output. This FIG. 8 reflects the known dependence of the PMT time response on voltage, and reveals the direction of the phase scale.

FIG. 9 shows the result obtained when a 515 nm high pass filter is used to pass fluorescence output signals from both Fluoresbrite™ particles and the EB-nuclei to the PMT. The EB-stained nuclei have a lower phase signal than the Fluoresbrite™ particles. Even for low signal intensities where the phase detector response is reduced, the particles are distinguished from the nuclei by using correlated phase/amplitude data. In these early measurements, the phase angle scale is arbitrary in direction and magnitude. Also, the change in phase with amplitude, accomplished here by changing the PMT voltage, is known for the time-response of PMT's. During a phase or modulation measurement the PMT voltage would be constant.

Figure 10:
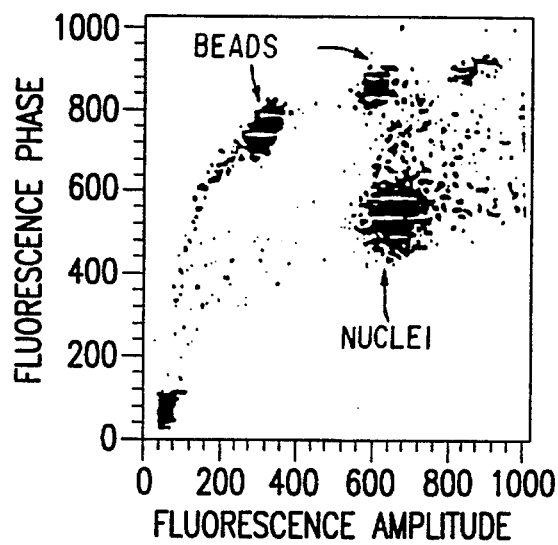
FIG. 10 is a graphical representation of phase fluorescence versus fluorescence amplitude of cell nuclei stained with ethidium bromide and fluorophore dyed particles with the use of an optical band pass filter with the PMT voltage held constant.

FIG. 10 shows the phase versus amplitude dot plot of the particle/nuclei mixture at a fixed PMT voltage. Particle doublets have nearly the same fluorescence amplitude as the G0/G1 nuclei but are easily resolved by their phase (fluorescence lifetime) difference.

As shown by the above-described data, the present invention provides for detection and characterization of cell component structure and composition based on changes in phase angle or modulation of signals corresponding to changes in lifetimes of at least one fluorophore associated with cells or particles used in a flow cytometer and methods according to the present invention.

What is claimed is:

1. A method of determining, in a flow cytometric environment, a fluorescence lifetime of at least one fluorophore associated with a cell or particle, comprising the steps of:

directing a stream of a plurality of said cells or particles past an observation point;

modulating a light source at a frequency of an input signal to produce modulated exciting light having a wavelength capable of exciting said at least one fluorophore;

irradiating at the observation point said cell or particle with said modulated light to produce emitted light from said at least one fluorophore;

detecting said emitted light and producing a corresponding modulated emission signal; and comparing said input signal and said modulated emission signal to produce an output signal corresponding to a difference between the phase and/or modulation of said modulated emission signal and said input signal, wherein said output signal is (a) indicative of a value of the fluorescence lifetime of said at least one fluorophore and (b) is independent of the intensity of the emitted light, and wherein said detecting step further comprises adjusting said output signal to reduce the effect of autofluorescence.

2. A method of determining, in a flow cytometric environment, a fluorescence lifetime of at least one fluorophore associated with a cell or particle, comprising the steps of:

directing a stream of a plurality of said cells or particles past an observation point;

modulating a light source at a frequency of an input signal to produce modulated exciting light having a wavelength capable of exciting said at least one fluorophore;

irradiating at the observation point said cell or particle with said modulated light to produce emitted light from said at least one fluorophore;

detecting said emitted light and producing a corresponding modulated emission signal; and comparing said input signal and said modulated emission signal to produce an output signal corresponding to a difference between the phase and/or modulation of said modulated emission signal and said input signal, wherein said output Signal is (a) indicative of a value of the fluorescence lifetime of said at least one fluorophore and (b) is independent of the intensity of the emitted light, and wherein the comparing step comprises dividing said input signal into first and second signals;

dividing said emission signal into third and fourth signals;

placing said first signal into phase quadrature with respect to said second signal;

mixing said first and third signals and said second and fourth signals, respectively, to generate fifth and sixth signals, respectively, that are in phase quadrature; and determining the ratio of said fifth and sixth signals in order to generate the value which is indicative of the fluorescence lifetime of said at least one fluorophore but which value is independent of intensity of said emitted light.

3. The method of claim 2, further comprising, prior to said mixing step, amplifying and limiting each of said first, second, third and fourth signals, respectively, by a corresponding amplifier and limiting circuit.

4. The method of claim 3, further comprising, prior to said determining step, filtering each of said fifth and sixth signals, respectively, by a corresponding low pass filter.

5. The method of claim 4, wherein said determining step comprises peak detecting said fifth and sixth signal after said filtering.

6. A method of determining, in a flow cytometric environment, a fluorescence lifetime of at least one fluorophore associated with a cell or particle, comprising the steps of:

directing a stream of a plurality of said cells or particles past an observation point;

modulating a light source at a frequency of an input signal to produce modulated exciting light having a wavelength capable of exciting said at least one fluorophore;

irradiating at the observation point said cell or particle with said modulated light to produce emitted light from said at least one fluorophore;

detecting said emitted light and producing a corresponding modulated emission signal; and comparing said input signal and said modulated emission signal to produce an output signal corresponding to a difference between the phase and/or modulation of said modulated emission signal and said input signal, wherein said output signal is (a) indicative of a value of the fluorescence lifetime of said at least one fluorophore and (b) is independent of the intensity of the emitted light, and wherein the comparing step comprises dividing said emission signal into first and second signals;

filtering (a) said first signal by a high pass filter, followed by amplifying and splitting said first signal into a third signal and a fourth signal and (b) said second signal with a low pass filter;

amplifying and limiting said input signal and limiting said third signal, respectively, by passing said input signal through a signal amplifier set at a preset level and a limiting circuit, and by passing said third signal through a limiting circuit; then mixing said third signal and said input signal, respectively, to generate a fifth signal; and determining the ratio of said second and fourth signals as a ratio signal; and comparing said ratio signal and said fifth signal in order to generate a value which is indicative of the fluorescence lifetime of said at least one fluorophore but which value is independent of the intensity of the emitted light.

7. The method of claim 6, wherein said input signal is provided by one selected from (a) receiving said modulated light by a photomultiplier tube and producing said input signal; and (b) a frequency generator set at said frequency.

8. A flow cytometer operative to measure a fluorescence lifetime of at least one fluorophore associated with a cell or a particle, comprising:

a flow chamber for directing a plurality of cells or particles past an observation point;

a light source modulated by a frequency of an input signal for irradiating, at said observation point, said cell or particle with modulated light having a wavelength capable of exciting said at least one fluorophore to produce emitted light;

a photodetector for detecting said emitted light and producing a corresponding emission signal; and a phase/modulation detector for generating an output signal corresponding to a difference between the phase and/or modulation of said emission signal and said input signal, wherein said output signal is (a) indicative of a value of the fluorescence lifetime of said at least one fluorophore and (b) is independent of the intensity of the emitted light, and wherein said apparatus further comprises:

a first power splitter for dividing said input signal into first and second signals having the same amplitude and frequency;

a second power splitter for dividing said emission signal into third and fourth signals, said signals having an equal amplitude and identical frequency;

a first phase shifter for providing a predetermined phase shift to said first signal;

first and second mixers, said first mixer receiving said first signal of said first power splitter and said third signal from said second power splitter and generating a fifth signal, said second mixer receiving said second signal and said fourth signal and generating a sixth signal;

a ratio unit for receiving said fifth signal and said sixth signal from said first mixer and said second mixer, respectively, and generating the ratio of said fifth signal and said sixth signal as said output signal.

9. The apparatus of claim 8 further comprising:

first, second, third and fourth amplifiers and limiters, respectively, for amplifying and limiting each of said first, second, third and fourth signals, respectively, prior to being fed into said first and second mixers.

10. The method of claim 9 further comprising:

first and second low pass filters, respectively, for filtering each of said fifth and sixth signals prior to said generating of said ratio.

11. The method of claim 8, further comprising, first and second peak detectors for peak detecting said fifth and sixth signals, respectively, after said filtering.

12. A flow cytometer operative to measure a fluorescence lifetime of at least one fluorophore associated with a cell or a particle, comprising:

a flow chamber for directing a plurality of cells or particles past an observation point;

a light source modulated by a frequency of an input signal for irradiating, at said observation point, said cell or particle with modulated light having a wavelength capable of exciting said at least one fluorophore to produce emitted light;

a photodetector for detecting said emitted light and producing a corresponding emission signal; and a phase/modulation detector for generating an output signal corresponding to a difference between the phase and/or modulation of said emission signal and said input signal, wherein said output signal is (a) indicative of a value of the fluorescence lifetime of said at least one fluorophore and (b) is independent of the intensity of the emitted light, and wherein said apparatus further comprises:

a first power splitter for dividing said emission signal into first and second signals, said signals having an equal amplitude and identical frequency;

a high pass filter for filtering said first signal;

a first amplifier and a second power splitter, respectively, for amplifying and splitting said first signal into a third signal and a fourth signal;

a first low pass filter for filtering said second signal;

a second amplifier and a first limiting circuit, respectively, for amplifying and limiting said input signal;

a second limiting circuit for limiting said third signal;

a mixer for mixing said third signal and said input signal, respectively, to generate a fifth signal;

a second low pass filter for filtering ,said fifth signal; and a ratio unit for determining the ratio of said second and fourth signals as a ratio signal;

wherein said phase/modulation detector is fed said ratio signal and said fifth signal to determine said output signal.

13. The method of claim 12 further comprising:

a photomultiplier tube for receiving said modulated light and producing said input signal.

14. The method of claim 12 further comprising:

a frequency generator for producing said input signal at said frequency.

15. A flow cytometer operative to measure a fluorescence lifetime of at least one fluorophore associated with a cell or a particle, comprising:

a flow chamber for directing a plurality of cells or particles past an observation point;

a light source modulated by a frequency of an input signal for irradiating, at said observation point, said cell or particle with modulated light having a wavelength capable of exciting said at least one fluorophore to produce emitted light;

a photodetector for detecting said emitted light and producing a corresponding emission signal; and a phase/modulation detector for generating an output signal corresponding to a difference between the phase and/or modulation of said emission signal and said input signal, wherein said output signal is (a) indicative of a value of the fluorescence lifetime of said at least one fluorophore and (b) is independent of the intensity of the emitted light, and wherein said apparatus further comprises:

an input optics system operative to shape and direct said modulated light to said observation point; and an output optics system operative to receive and direct said emitted light onto said photodetector.

16. A flow cytometer operative to measure a fluorescence lifetime of at least one fluorophore associated with a cell or a particle, comprising:

a flow chamber for directing a plurality of cells or particles past an observation point;

a light source modulated by a frequency of an input signal for irradiating, at said observation point, said cell or particle with modulated light having a wavelength capable of exciting said at least one fluorophore to produce emitted light;

a photodetector for detecting said emitted light and producing a corresponding emission signal; and a phase/modulation detector for generating an output signal corresponding to a difference between the phase and/or modulation of said emission signal and said input signal, wherein said output signal is (a) indicative of a value of the fluorescence lifetime of said at least one fluorophore and (b) is independent of the intensity of the emitted light, and wherein said apparatus further comprises:

a variable phase shifter operative to shift the phase of said input signal.

17. The apparatus of claim 16 wherein said variable phase shifter is operative to reduce the effect of autofluorescence.

18. The apparatus of claim 17 wherein signals contributed by said autofluorescence are reduced substantially to zero.

* * * * *

UNITED STATES PATENT AND TRADEMARK OFFICE
CERTIFICATE OF CORRECTION

PATENT NO. : 5,504,337
DATED : April 2, 1996
INVENTOR(S) : Joseph R. Lakowicz et al.

It is certified that error appears in the above-indentified patent and that said Letters Patent is hereby corrected as shown below:

Col. 12, line 13, "R=tanD=2$\pi$.f.T" should be -- R=tanD=2$\pi$.f.$\tau$ --; Col. 12, last line, "T" should be -- $\tau$ --; Col. 15, line 26, "T=(tan(phase" should be -- $\tau$=(tan(phase --; Col. 16, line 66, "de" should be -- made --; In the Claims: Col. 19, line 5 (claim 2), "Signal" should be -- signal --.

Signed and Sealed this

Seventeenth Day of September, 1996

*Attest:*

BRUCE LEHMAN

*Attesting Officer*     *Commissioner of Patents and Trademarks*